United States Patent

Bowden et al.

Patent Number: 5,527,972
Date of Patent: Jun. 18, 1996

[54] PREPARATION AND USE OF HALOGENATED ALCOHOLS

[75] Inventors: Martin C. Bowden, Brighouse; Michael D. Turnbull, Reading, both of United Kingdom

[73] Assignee: Zeneca Limited, London, England

[21] Appl. No.: 249,783

[22] Filed: May 26, 1994

[30] Foreign Application Priority Data

May 28, 1993 [GB] United Kingdom ............... 9311142

[51] Int. Cl.$^6$ .................................................. C07C 33/025
[52] U.S. Cl. ............................................................. 568/843
[58] Field of Search ................................................ 568/843

[56] References Cited

U.S. PATENT DOCUMENTS

4,532,020  7/1985  Ishikawa et al. ..................... 568/843

FOREIGN PATENT DOCUMENTS

2076804  12/1981  United Kingdom.

OTHER PUBLICATIONS

CA 108: 22101j; Tamejiro Hiyama et al.; Jan. 18, 1988; "1–Substituted 2,2–dihalo–3,3,3–trifluoropropanols as intermediates for pyrethroid insecticides".

CA 108: 94064x; Tamejiro Hiyama et al., Apr. 14, 1988; "1,1,1–Trifluoro–2,2–dihalo–5–methyl–4–hexen–3–ols and their derivatives".

H. Kropf et al., "Methoden der Organischen Chemie Teil 2, Band 6/1A; Edition 4", 1981, Thieme Verlag, de, Stuttgart, pp. 1334–1337.

*Primary Examiner*—Rebecca Cook
*Attorney, Agent, or Firm*—Joel G. Ackerman

[57] ABSTRACT

The invention discloses a process for the preparation of a halogenated alcohol of formula:

$$CF_3-CXCl-CH(OH)-CH=C(CH_3)_2$$

wherein X is bromo or chloro which comprises reacting a compound of formula:

$$CF_3CHXCl$$

with 3-methylbut-2-en-1-al in the presence of a strong base and an inert solvent. The products are useful intermediates for the manufacture of insecticides.

7 Claims, No Drawings

PREPARATION AND USE OF HALOGENATED ALCOHOLS

This invention relates a novel process for making certain halogenated alcohols useful in the synthesis of valuable pesticide intermediates.

Esters of 3-(2-chloro-3,3,3-trifluoroprop-1-en-1-yl)-2,2-dimethylcyclopropane carboxylic acid with for example 3-phenoxybenzyl alcohol, α-cyano-3-phenoxybenzyl alcohol and 2-methyl-3-phenylbenzyl alcohol are important insecticidal and acaricidal products, and the sidle alkyl esters of this acid are important intermediates in the manufacture of such products. It is desirable to establish novel processes for the manufacture of such intermediates in order to increase the manufacturer's flexibility to respond to fluctuations in price and availability of raw materials.

The present invention relates to a novel process for providing certain halogenated alcohols which can be used in a novel synthetic procedure to obtain the above-mentioned acid and its esters.

Accordingly the invention provides a process for preparing a compound of formula (I): wherein X is chloro or bromo which comprises reacting a compound of formula (II) with 3-methylbut-2-en-1-al in the presence of a strong base and an inert solvent.

Where the compound of formula (I) is 5,5-dichloro-4-hydroxy-2-methyl-6,6,6-trifluorohex-2-ene the compound of formula (II) is 1,1-dichloro-2,2,2-trifluoroethane.

Where the compound of formula (I) is 5-bromo-5-chloro-4-hydroxy-2-methyl-6,6,6-trifluorohex-2-ene the compound of formula (II) is 1-bromo-1-chloro-2,2,2-trifluoroethane. 5-Bromo-5-chloro-4-hydroxy-2-methyl-6,6,6-trifluorohex-2-ene appears not to have been previously described, so in a further aspect this invention provides 5-bromo-5-chloro-4-hydroxy-2-methyl-6,6,6-trifluorohex-2-ene as a novel compound.

The process is conducted in the presence of a strong base, which is believed to act by generating a perhaloalkyl ion which then reacts with the aldehyde. Suitable strong bases include alkali metal lower alkoxides, such as sodium or potassium isopropoxides or t-butoxides, but other bases such as alkali metal disilylazides may also be used.

The process is preferably conducted at lower temperatures to avoid the production of unwanted by-products. A preferred temperature is within the range −80° C. to 0° C., especially where a polar aprotic solvent is used. The process can be operated in a batch-wise or continuous manner. When operated as a a continuous process manner the reactants are fed in controlled way to a cooled solution or suspension of the base in the solvent. The reaction is very rapid especially at temperatures within the range −40° to 0° C. Particular examples of polar aprotic solvents which may be useful in the process include amides such as dimethylformamide, dimethylacetamide and di-n-butylacetamide, cyclic ethers such as tetrahydrofuran, tetrahydropyran and dioxan, glycol ethers such as ethylene glycol dimethyl ether, and ethylene glycol diethyl ether, and sulphoxides such as dimethyl sulphoxide. However other inert solvents such as aromatic hydrocarbons e.g. toluene may also be used. Tetrahydrofuran is particularly effective especially when the base is used in the form of a solution of an alkali metal alkoxide such as sodium t-butoxide in dimethylformamide.

The process is useful to produce the compounds of formula (I) in good yield and purity and allows for easy isolation of the desired product. Any unreacted or excess compound of formula (II) can be readily recovered and recycled.

The compounds of formula (I) may be used in the synthesis of 3-(2-chloro-3,3,3-trifluoroprop-1-en-1-yl)-2,2-dimethylcyclopropane carboxylic acid or an ester thereof with a lower alkanol, such as the methyl or ethyl ester, which comprises the steps of (a) reacting a compound of formula (I) with a tri-lower-alkyl orthoacetate containing up to four carbon atoms in each alkyl group in the presence of at least a catalytic amount of a acid to obtain a compound of formula (III) where R is alkyl of up to four carbon atoms, (b) treating said compound of formula (III) with at least one molar equivalent of a base to obtain a lower alkyl ester of 3-(2-chloro-3,3,3-trifluoroprop-1-en-1-yl )-2,2-dimethylcyclopropane carboxylic acid, and (c) thereafter, if desired, subjecting said lower alkyl ester to hydrolysis to obtain the said carboxylic acid.

Preferably the tri-lower-alkyl orthoacetate is selected from trimethyl orthoacetate and triethyl orthoacetate.

The acid used in step (a) is preferably a simple carboxylic acid such as a propionic acid or butyric acid, e.g. isobutyric acid, or an alkane arene sulphonic acid e.g. p-toluene sulphonic acid. The process is carried out at an elevated temperature preferably the reflux temperature, under conditions where alcohol generated by the process can be removed from the reaction zone.

The base used in step (b) is preferably a alkali metal alkoxide, and the process may be carried out in a suitable solvent or diluent such as for example a polar aprotic solvent such as dimethylformamide or an excess of the alcohol corresponding to the alkali metal alkoxide. Sodium or potassium t-butoxide are preferred bases and the reaction is preferably carried out in dimethylformamide.

Further particulars concerning the process is by which the compounds of formula (I) can be made and used in the synthesis of esters of 3-(2-chloro-3,3,3-trifluoroprop-1-en-1-yl)-2,2-dimethylcyclopropane carboxylic acid are set out in the Examples below.

In step (a) of the above process the reaction of the compound of formula (I) with the trialkyl orthoacetate is believed to lead initially to a compound of formula (IV) where X is chloro or bromo and R is alkyl of up to four carbon atoms. Such compounds are believed not to have been previously described and in particular the following specific compounds are believed to be novel:

5-bromo-5-chloro-4-(1,1-diethoxyethoxy)-2-methyl-6,6,6-trifluorohex-2-ene,
5,5-dichloro-4-(1-diethoxyethoxy )-2-methyl-6,6,6-trifluorohex-2-ene,
5-bromo-5-chloro-4-(1,1-dimethoxyethoxy)-2-methyl-6,6,6-trifluorohex-2-ene, and
5,5-dichloro-4-(1,1-dimethoxyethoxy)-2-methyl-6,6,6-trifluorohex-2-ene.

Under the process conditions the compounds of formula (IV) undergo a rearrangement leading to the compounds of formula (III). The compounds of formula (III) are also believed not to have been described previously and in particular the following specific compounds are believed to be novel= ethyl 6-bromo-6-chloro-3,3-dimethyl-7,7,7-trifluorohept-4-enoate,
methyl 6-bromo-6-chloro-3,3-dimethyl-7,*,7-trifluorohept-4-enoate,
ethyl 6,6-dichloro-3,3-dimethyl-7,7,7-trifluorohept-4-enoate, and
methyl 6,6-dichloro-3,3-dimethyl-7,7,7-trifluorohept-4-enoate.

The process of the invention is illustrated by the following Examples.

EXAMPLE 1

This Example illustrates the preparation of 5,5-dichloro-4-hydroxy-2-methyl-6,6,6-trifluoro hex-2-ene.

Sodium t-butoxide (2.4ml of a 42% solution in dry dimethylformamide) was added dropwise over a period of 20 minutes to a stirred mixture of 1,1-dichloro-2,2,2-trifluoroethane (1.38 g), 3-methylbut-2-ene-1-al (0.636 g) and dry tetrahydrofuran (30 ml) maintained at a temperature of −65° C. by external cooling under a nitrogen atmosphere, and the stirred mixture maintained at that temperature for a further 30 minutes after completion of the addition. The external cooling was removed and the reaction quenched by dropwise addition of a saturated aqueous ammonium chloride solution until the temperature had risen to −20° C. The mixture was thereafter stirred until the temperature had risen to ambient (ca. 20° C.).

The aqueous and organic phases were separated and the aqueous phase extracted with dichloromethane (2×20 ml) and the extracts combined with the organic phase and dried over anhydrous sodium sulphate. After removal of the solvents by evaporation under reduced pressure the residue was dissolved in hexane (20 ml) and the solution washed with brine (3×5 ml) and dried over anhydrous sodium sulphate, and concentrated by removal of the solvent under reduced pressure. The residue was dissolved in a mixture of ethyl acetate and petroleum ether (boiling range 40°–60° C.) (1:5 parts by volume, 20 ml) and purified by loading onto a short silica column (3.75 cm) and eluting with the same mixture (400 ml). Successive fractions (3) were examined by chromatography to establish that the desired product was present in the first two fractions. The eluate was concentrated by evaporation of the solvents under reduced pressure and the residue (1.33 g) identified by nuclear magnetic resovance spectroscopy and gas chromatographic-mass spectral analysis as 5,5-dichloro-4-hydroxy-2-methyl-6,6,6-trifluorohex-2-ene.

EXAMPLE 2

This Example illustrates the preparation of 5-bromo-5-chloro-4-hydroxy-2-methyl-6,6,6-trifluorohex-2-ene.

Sodium t-butoxide (1.39 g of a 42% solution in dry dimethyl formamide was added dropwise over a period of 5 minutes to a stirred mixture of 1-bromo-1-chloro-2,2,2-trifluoroethane (0.535 ml), 3-methylbut-1-en-1-al (0.538 ml) and dry tetrahydrofuran (10 ml) maintained at a temperature of −78° C. by external cooling under a nitrogen atmosphere. The mixture was then stirred for a further 40 minutes at the temperature after which the external cooling was removed and the reaction quenched by the dropwise addition of saturated aqueous ammonium chloride solution. The mixture was then partitioned between water and diisopropyl ether and the aqueous phase separated, washed with diisopropyl ether (3×25ml), and the washings combined with the organic phase. The organic phase was washed with brine and dried over anhydrous sodium sulphate and concentrated by evaporation under reduced pressure. After purification by a procedure similar to that set out in the previous Example there was obtained 5-bromo-5-chloro-4-hydroxy-2-methyl-6,6,6-trifluorohex-2-ene (1.39 g), identified by nuclear magnetic resonance and infra-red spectroscopy.

This Example illustrates the preparation of 5-bromo-5-chloro-4-hydroxy-2-methyl-6,6,6-trifluorohex-2-ene.

Tetrahydrofuran (230 ml) and sodium t-butoxide (57.6 g; 40% w/v solution in dimethylformamide) was charged to a split-neck reaction flask, and cooled to −60° C. with stirring. 1-Bromo-1-chloro-2,2,2-trifluorethane (47.6 g) and senecialdehyde (20.9 g) were charged simultaneously over 25 minutes, then the mixture was stirred at −60° C. for a further 30 minutes. On completion of reaction, the mass was quenched by controlled addition of saturated ammonium chloride solution (120 ml). Hexane (500 ml) was added to the mixture, then the aqueous phase was separated and extracted with further hexane (2×500 ml). The combined organics were washed with brine (2×100 ml) and then water (3×20 ml). Drying (sodium sulphate) and concentration in vacuo then gave the product 5-bromo-5-chloro-4-hydroxy-2-methyl-6,6,6-trifluorohex-2-ene as a mobile yellow oil (50.1 g, 70% yield).

$^1$H NMR: 1.30(3H,s,:CMe$_2$); 1.35(3H,s,:CMe); 1.85(1H, br,OH); 4.20 and 4.30(1H,d,CHOH diastereomers): 4.90 g (1H,d,:CH). MS: 195 (CF$_3$CClBr+), 85 (M+−CF$_3$CClBr). IR: 3400 cm$^{-1}$.

EXAMPLE 4

This Example illustrates the preparation of 5-bromo-5-chloro-4-(1,1-dimethoxyethoxy)-2-methyl-6,6,6-trifluorohex-2-ene 5-Bromo-5-chloro-4-hydroxy-2-methyl-6,6,6-trifluorohex-2ene (10.0 g), trimethyl orthoacetate (48.0 g) and isobutyric acid (0.29 g) were charged to a round-bottomed flask fitted with: nitrogen inlet/bubbler, thermometer and Dean and Stark received packed with 5A molecular seives. The mixture was heated with agitation to reflux and distillates collected until reaction mass temperature increased to 111° C. (ca. 1 hr). Once the reaction was complete, the residual trimethyl orthoacetate was removed by distillation under vacuum (ca. 50° C. ≃50 mmHg) to give the product, 5-bromo-5-chloro-4 -1,1-dimethoxyethoxy)-2-methyl-6,6,6-trifluorohex-2-ene, as an orange oil (10.9 g, 85% yield).

$^1$H NMR 1.45(3H,s:MeCOMe); 1.75(3H,s:CMe$_2$); 1.85 (3H,s:CMe$_2$); 3.28(3H, OMe); 3.30(3H,s,OMe); 4.98 and 5.02 (1H,d, CHOR-diastereomers); 5.35(1H,d,:CH). MS: 89 g (MeC(COMe)$_2$+).

EXAMPLE 5

This Example illustrates the preparation of methyl 6-bromo-6-chloro-3,3-dimethyl-7,7,7-trifluorohex-4-enoate, 5-Bromo-5-chloro-4-hydroxy-2-methyl-6,6,6-trifluorohex-2-ene (10.0 g), trimethyl orthoacetate (16.0 g) and Montmorillonite KSF (0.5 g) were charged to a round-bottomed flask fitted with: nitrogen inlet/bubbler, thermometer and still-head. The mixture was heated with agitation, and the methanol-trimethyl orthoacetate distillates were collected until the reactor temperature increased to 111° C. (ca. 1 hr). The reaction was then heated to 135° C. and held for a further 1 hour. The methanol/trimethyl orthoacetate distillates were recharged and the distillation procedure repeated twice. Once the reaction was complete, the Montmorillonite was removed by filtration. The residual trimethyl orthoacetate was then removed by distillation under vacuum (ca. 50° C. ≃100 mmHg) to give the product, methyl 6-bromo-6-chloro-3,3-dimethyl-7,7,7-trifluorohept-4-enoate as a brown oil (7.8 g, 59 g yield).

$^1$H NMR: 1.20(6H,s,CMe$_2$); 2.40 (2H,s,CH$_2$CO$_2$Me); 3.65(3H,s,OMe); 5.75(1H,d,CH); 6.45(1H,d,CH). MS: 305(M$^+$−OMe); 257 (M+−Br), IR: 1750 cm$^{-1}$.

EXAMPLE 6

This Example illustrates the preparation of ethyl 6,6-dichloro-3,3-dimethyl-7,7,7-trifluorohept-4-enoate.

A mixture of triethyl orthoacetate (25 ml), 5,5-dichloro-4-hydroxy-2-methyl-6,6,6-trifluorohex-2-ene (3.5 g), and isobutyric acid (0.11 g) was heated at the reflux temperature. The refluxing volatiles were condensed and collected in a Dean & Stark apparatus containing molecular sieves (4A) to collect the by-product ethanol and separate it from the orthoacetate which was returned to the mixture. After 30 minutes the more volatile components were removed by evaporation under reduced pressure and the residual oil (consisting principally of 5,5-dichloro-4-(1,1-diethoxyethoxy)-2-methyl-6,6,6-trifluorohex-2-ene, 3.8 g) collected. This was then heated with isobutyric acid (10 μl) at the reflux temperature for 16 hours under a condenser containing molecular sieves (4A) to remove ethanol from the condensate. The residual oil was subjected to purification by column chromatography using a 15:1 (by volume) mixture of hexane:ethyl acetate as eluant and a silica gel column (230–400 mesh, 60 Å) to obtain ethyl 6,6-dichloro-3,3-dimethyl-7,7,7-trifluorohept-enoate, identified by nuclear magnetic resonance, and gas chromatographic mass-spectroscopy.

EXAMPLE 7

This Example illustrates the preparation of methyl 6,6-dichloro-3,3-dimethyl-7,7,7-trifluorohept-4-enoate.

A procedure similar to that described in Example 6 was used to obtain the product from a mixture of trimethyl orthoacetate (70 ml), 5,5-dichloro-4-hydroxy-2-methyl-6,6,6-trifluorohex-2-ene (10 g) and isobutyric acid (0.37 g).

EXAMPLE 8

This Example illustrates the preparation of ethyl 3-(2-chloro-3,3,3-trifluoroprop-1-en-1-yl)-2,2-dimethylcyclopropane carboxylate.

A stirred solution of ethyl 6,6-dichloro-3,3-dimethyl-7,7,7-trichlorohept-4-enoate (0.1 g) in dimethylformamide (10 ml) was cooled to −25° C. under a nitrogen atmosphere and sodium t-butoxide (0.1 ml of a solution in dimethylformamide) added dropwise. After 30 minutes five further drops of the sodium t-butoxide solution was added and the mixture stirred for a further 15 minutes, before the reaction was quenched with saturated ammonium chloride solution (2 ml) over a 10 minutes period. Water (40 ml) was added and the mixture extracted with hexane (3×40 ml) the combined extracts washed with brine (20 ml) and dried over anhydrous sodium sulphate. The dried solution was filtered and concentrated by evaporation under reduced pressure to give ethyl 3-(2-chloro-3,3,3-trifluoroprop-1-en -1-yl)-2,2-dimethylcyclopropane carboxylate as a mixture of isomers.

EXAMPLE 9

This Example illustrates the preparation of methyl 3-(2-chloro-3,3,3-trifluoroprop-1-en-1-yl)-2,2-dimethylcyclopropane carboxylate.

By the use of a procedure similar to that described in the previous example the desired product was obtained by treating a solution of methyl 6,6-dichloro-3,3-dimethyl-7,7,7-trifluorohept-4-enoate (0.217 g) in dry dimethylformamide (10 ml) at 0° C. under a nitrogen atmosphere with sodium t-butoxide (0.2 ml of a 42% solution in dimethylformamide). The identity of the product was confirmed by gas chromatographic mass spectroscopy as consisting principally of methyl cis-3-(Z-2-chloro-3,3,3-trifluoroprop-1-en-1-yl)-2,2-dimethyl cyclopropane carboxylate.

CHEMICAL STRUCTURES
(in description)

$$CF_3-CXCl-CH(OH)-CH=C(CH_3)_2 \quad (I)$$
$$CF_3-CHXCl \quad (II)$$
$$CF_3-CXCl-CH=CH-C(CH_3)_2-CH_2CO_2R \quad (III)$$

$$CF_3-CXCl-\underset{\underset{CH_3}{|}}{\underset{O-C(OR)_2}{|}}\overset{\overset{CH=C(CH_3)_2}{|}}{CH} \quad (IV)$$

We claim:

1. A process for the preparation of a halogenated alcohol of formula:

$$CF_3-CXCl-CH(OH)-CH=C(CH_3)_2$$

wherein X is bromo or chloro which comprises reacting a compound of formula:

$$CF_3CHXCl$$

with 3-methylbut-2-en-1-al in the presence of a strong base selected from an alkali metal lower alkoxide and an alkali metal disilylazide and an inert solvent.

2. A process for preparing a halogenated alcohol as defined in claim 1 wherein the strong base is an alkali metal lower alkoxide.

3. A process as claimed in claim 1 wherein the inert solvent is a polar aprotic solvent.

4. A process as claimed in claim 1 conducted at a temperature within the range −80° C. to 0° C.

5. A process for the preparation of 5,5-dichloro-4-hydroxy-2-methyl-6,6,6-trifluorohex-2-ene which comprises reacting 1,1-dichloro-2,2,2-trifluoroethane with 3-methylbut-2-en-1-al in the presence of a strong base selected from an alkali metal lower alkoxide and an alkali metal disilylazide and a polar aprotic solvent.

6. A process as claimed in claim 5 wherein the strong base is an alkali metal lower alkoxide.

7. A process as claimed in claim 6 wherein the alkali metal alkoxide is sodium or potassium t-butoxide.

* * * * *